(12) United States Patent
Watchmaker et al.

(10) Patent No.: US 12,728,028 B2
(45) **Date of Patent: *Sep. 8, 2026**

(54) ANGULAR DIGITAL DEVICE FOR JOINT DEFORMITY OR IMBALANCE

(71) Applicants: Greg Watchmaker, Mequon, WI (US); Randy Dahl, Sussex, WI (US)

(72) Inventors: Greg Watchmaker, Mequon, WI (US); Randy Dahl, Sussex, WI (US)

( * ) Notice: Subject to any disclaimer, the term of this patent is extended or adjusted under 35 U.S.C. 154(b) by 9 days.

This patent is subject to a terminal disclaimer.

(21) Appl. No.: 18/957,795

(22) Filed: Nov. 24, 2024

(65) Prior Publication Data

US 2025/0161091 A1 May 22, 2025

Related U.S. Application Data

(63) Continuation of application No. 17/576,093, filed on Jan. 14, 2022, now Pat. No. 12,232,995.

(51) Int. Cl.
*A61F 5/10* (2006.01)
*A61F 5/01* (2006.01)

(52) U.S. Cl.
CPC ................ *A61F 5/10* (2013.01); *A61F 5/013* (2013.01); *A61F 2005/0153* (2013.01); *A61F 2005/0165* (2013.01)

(58) Field of Classification Search
CPC ...... A61F 2005/0153; A61F 2005/0165; A61F 5/013; A61F 5/10; A61F 5/0123; A61F 5/05875; A61B 2017/584; A61B 17/56
See application file for complete search history.

(56) References Cited

U.S. PATENT DOCUMENTS 135,305 A * 1/1873 Ranney
167,894 A 9/1875 Hale, et al.
523,069 A 7/1894 Grasinger
2,461,970 A * 2/1949 Finegan ................ A61F 13/105 2/21
2,740,121 A * 4/1956 Robert .................. A61F 13/105 2/21
3,794,019 A 2/1974 Ritland
4,243,026 A 1/1981 Barber
4,441,489 A 4/1984 Evans
4,507,804 A * 4/1985 Consigny ............. A41D 13/087 2/21
4,763,940 A * 8/1988 Held .................... A41D 13/087 2/21
4,829,988 A * 5/1989 Caminiti ................ A61H 1/008 602/22
5,095,897 A 3/1992 Clark
5,230,699 A * 7/1993 Grasinger ........... A61F 5/05866 128/880

(Continued)

*Primary Examiner* — Camtu T Nguyen

(57) ABSTRACT

Embodiments of the inventive concepts disclosed herein are directed to an angular digital device for joint deformity or imbalance. A device formed from a soft material shaped to fit a digit with straight segments and angled transitions at the interphalangeal joint levels such that rotational force(s) are created at the joint line(s). Additionally, an 'open transition' design with a dorsal strap element is described, and a design with an additional moldable, semi-rigid component added. A retention strap is described to prevent the splint from migrating off during sleep.

9 Claims, 6 Drawing Sheets

(56) References Cited

U.S. PATENT DOCUMENTS

| | | | | |
|---|---|---|---|---|
| 5,383,846 | A * | 1/1995 | Short | A41D 13/087 602/61 |
| 5,517,692 | A * | 5/1996 | Wunderlich-Kehm | A45D 29/00 132/73 |
| 5,947,915 | A | 9/1999 | Thibodo | |
| 6,532,963 | B2 * | 3/2003 | Swanbeck | A41D 13/087 128/880 |
| 6,839,905 | B1 * | 1/2005 | Bruder | A41D 13/087 2/21 |
| 7,251,836 | B2 * | 8/2007 | Santiago | A41D 13/087 2/21 |
| 8,490,215 | B2 * | 7/2013 | Mueller | A41D 19/01588 2/21 |
| 10,709,595 | B2 | 7/2020 | Hornsby | |
| D900,662 | S * | 11/2020 | LoPachin | D11/27 |
| 12,232,995 | B1 * | 2/2025 | Watchmaker | A61F 5/013 |
| 2004/0002673 | A1 | 1/2004 | Ferraioli | |
| 2004/0045071 | A1 * | 3/2004 | Robins | A41D 13/087 2/21 |
| 2007/0167894 | A1 * | 7/2007 | Ryscavage | A61F 5/0118 602/22 |
| 2011/0245747 | A1 | 10/2011 | Wollstein | |

* cited by examiner

ANGULAR DIGITAL DEVICE FOR JOINT DEFORMITY OR IMBALANCE

CROSS-REFERENCE TO RELATED APPLICATION

This application is a continuation of U.S. application Ser. No. 17/576,093, filed on Jan. 14, 2022, and now U.S. Pat. No. 12,232,995 issued on Feb. 25, 2025, and claims the benefit of and priority to the subject matter disclosed therein for all purposes.

BACKGROUND

This invention belongs to a class of devices that treat injured, stiff, or congenitally deformed finger joints. These devices function by creating rotational forces on the finger joints over an extended period of time in order to stretch contracted tissue that has resulted in a flexion or extension contracture at the interphalangeal joints and thus restore more functional range of finger motion.

Previously described finger sleeves and tubes are either of a straight (10709595, Hornsby) or gentle curved tube design (5095897, Clark and US2011/0245747, Wollstein). Additional non-tube devices utilize rigid wire spring and pad constructs (4243026A Barber and 4441489 Evans) or utilize strap constructs (3794019 Ritland) that provide corrective forces utilizing discrete small areas of contact with the finger.

Prior designs have drawbacks that the current invention solves. Prior tube designs of straight or gentle curved design are not formed with angles placed at the axis of rotation of the joint to be treated. Gently curved tubes in the shape of a banana or bow are not designed to isolate the corrective force at the intended joint axis. The current invention overcomes this drawback through the design of straight segments and angled transition(s) at the joint line(s) of the digit to create rotational forces in either a flexion or extension direction at the correct point along the digit. The current invention also improves upon prior tube designs that do not incorporate moldable segments that permit the rotational forces to be increased or decreased to suit the individual joint deformity The current invention avoids prior design drawbacks that incorporate an inverted internal seam to create the curved contour. The thick internal seam protrudes and creates a concentrated line of higher pressure with the skin that can limit wearer comfort and use.

The current invention also overcomes areas of high skin pressure that are associated with previous designs that utilize springs or straps and small discrete areas of contact. High contact pressure over a smaller area of skin risks skin sores and ulceration. Low contact area pad or strap constructs of prior designs also do not have the benefit of circumferential compression to reduce swelling of the injured finger. The current invention combines the advantage of circumferential compression to reduce swelling along with rotational correction at the axis of joint rotation.

An additional limitation of prior devices is that when worn overnight, prior devices migrate off the finger or are removed by the wearer inadvertently while sleeping. The current invention includes an optional wrist strap device with a hook and loop material that reduces migration during sleep.

Prior tube designs also have drawbacks when treating severely contracted joints that do not permit application of the prefabricated, fully formed tube over the contracted joint. The current invention includes an 'open transition' design variation wherein the tube has a partial opening that permits device application over the contracted joint followed by force application using an adjustable dorsal strap after the device is applied to the digit. The opening over the joint in this device design, therefore provides a means to apply the device before the corrective rotational force is first applied.

SUMMARY

In one aspect, the embodiments for the inventive concepts disclosed herein are directed to:

A device, shaped to fit a digit and made of two or more straight tubular segments of a stretchable material to fit the digit with at least one angled transition at the level of the interphalangeal joints. The device has a smooth interior surface to provide circumferential compression and may have a removable strap to secure it in place. The device may contain a moldable, semi-rigid angled element added to modify the rotational forces created by the stretchable material at the transition.

An 'open transition' device is described wherein an open transition between the straight tubular segments allows the device to be fitted to a severely contracted joint that may not otherwise permit application of a device where the angled transition is prefabricated. This design includes a connecting element that is tensioned after the splint has been applied. The device has a smooth interior surface to provide circumferential compression and may have a removable strap to secure it in place. The device may contain a moldable, semi-rigid angled element added to modify the rotational forces created by the stretchable material at the transition.

A device fabricated from neoprene, created by joining opposite edges of a sheet of neoprene to itself to form two straight tubular segments and an angled transition at the level of the proximal interphalangeal joint of a finger, to create a rotational force. The device has a smooth interior surface to provide circumferential compression and may have a removable strap to secure it in place. The device may contain a moldable, semi-rigid angled element added to modify the rotational forces created by the stretchable material at the transition.

BRIEF DESCRIPTION OF THE DRAWINGS

Implementations of the inventive concepts disclosed herein may be better understood when consideration is given to the following detailed description thereof. Such description makes reference to the included drawings, which are not necessarily to scale, and in which some features may be exaggerated and some features may be omitted or may be represented schematically in the interest of clarity. Like reference numerals in the drawings may represent and refer to the same or similar element, feature, or function. In the drawings.

DETAILED DESCRIPTION

Figure 1:
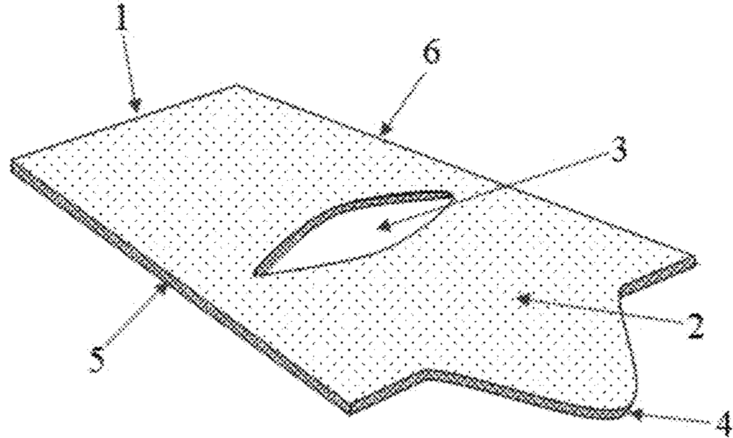
FIG. 1 is a drawing of the first step in constructing an angular digital device for joint deformity or imbalance in accordance with some embodiments of the inventive concepts disclosed herein.

Before describing in detail embodiments of the inventive concepts disclosed herein, it should be observed that the inventive concepts disclosed herein include but are not limited to a novel structural combination of components and circuits, and not to the particular detailed configurations thereof. Accordingly, the structure, methods, functions, control and arrangement of components and circuits have, for the most part, been illustrated in the drawings by readily understandable block representations and schematic diagrams, in order not to obscure the disclosure with structural details which will be readily apparent to those skilled in the art, having the benefit of the description herein. Further, the inventive concepts disclosed herein are not limited to the particular embodiments depicted in the schematic diagrams, but should be construed in accordance with the language in the claims.

The device may be used for congenital and acquired conditions of the digits whereby joint contracture and stiffness and digit swelling compromise function. The essential functions of the various embodiments of the device are to provide rotational corrective forces centered at the level of the interphalangeal joints in addition to compression to reduce swelling of the digit.

The various elements of the device function through the construction of straight, slightly tapered tubular segments over the phalanges using a stretchable material along with transition points at the interphalangeal joints as described herein.

Figure 2:
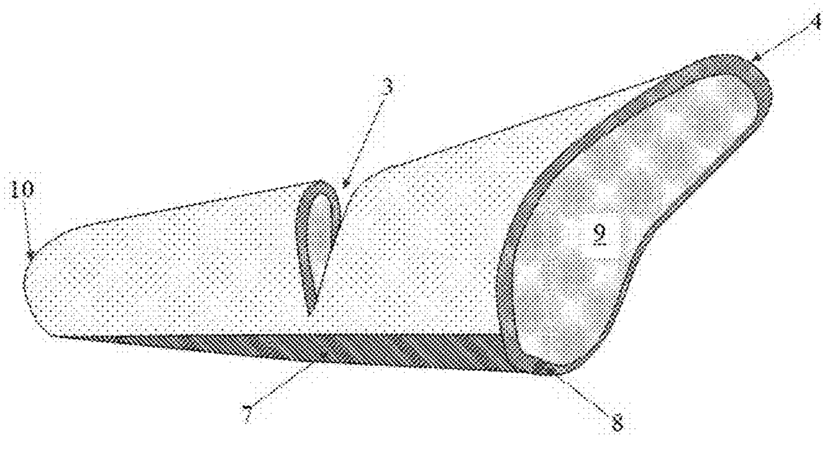
FIG. 2 is a drawing of the second step in constructing an angular digital device for joint deformity or imbalance in accordance with some embodiments of the inventive concepts disclosed herein.
Figure 3:
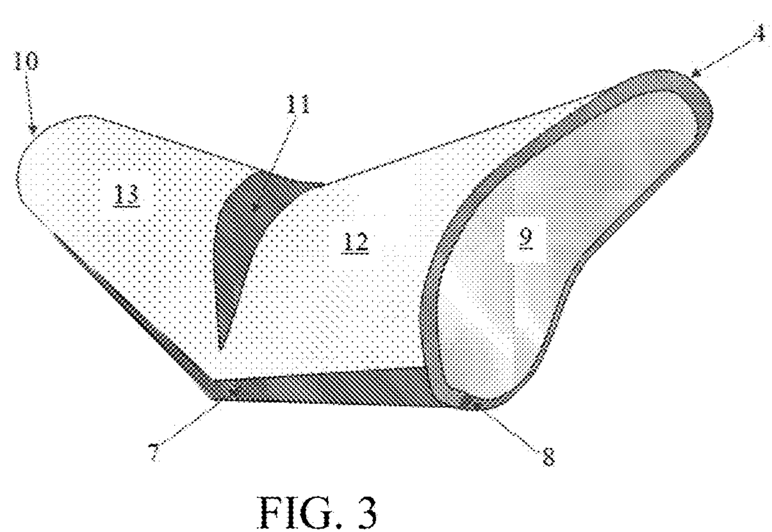
FIG. 3 is a drawing of the completed construction of an angular digital device for joint deformity or imbalance in accordance with some embodiments of the inventive concepts disclosed herein.

By way of example and referring to FIGS. 1-3, one embodiment of the device may be created from a flat sheet of 5 mm neoprene with fabric on both sides of the neoprene material with the distal edge 1 tapered relative to the proximal aspect of the device 2 in order to create a slightly tapered tubular opening when the device is fully formed. An elliptical piece of material has been removed 3 which upon final construction will create the angled transition between the straight tubular segments. An elongated extension of the proximal edge 4 assists with donning the device on a digit.

The tubular shape of the device is created by bonding the long edge 5 of the neoprene together with the opposite long edge 6 using an adhesive glue or heat activated seaming tape 7. The smooth seam 8 thus created on the inside of the tube aids in circumferential compression and avoids a raised ridge that would otherwise cause localized pressure on the skin. The larger proximal opening 9 and smaller distal opening 10 are shaped to fit a digit with an extended edge 4 to aid the wearer in donning the device. The elliptical dorsal opening 3 is closed in the third step of the device creation using adhesive glue or heat activated seaming tape 11 to create the angled transitional element between the proximal 12 and distal 13 straight tubular segments. This finished embodiment maintains the smooth volar seam 8, larger proximal opening 9, smaller distal opening 10 shaped to fit a digit with an extended edge 4 to aid the user in donning the device.

Figure 4:
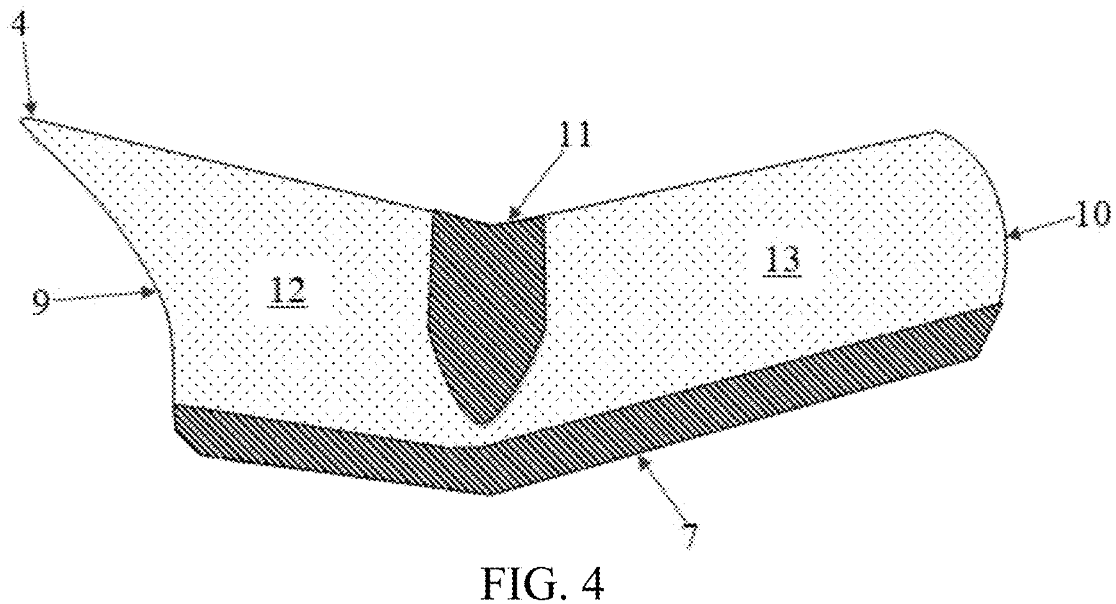
FIG. 4 is a side view drawing of one embodiment of the inventive concepts disclosed herein with a taped dorsal seam.
Figure 5:
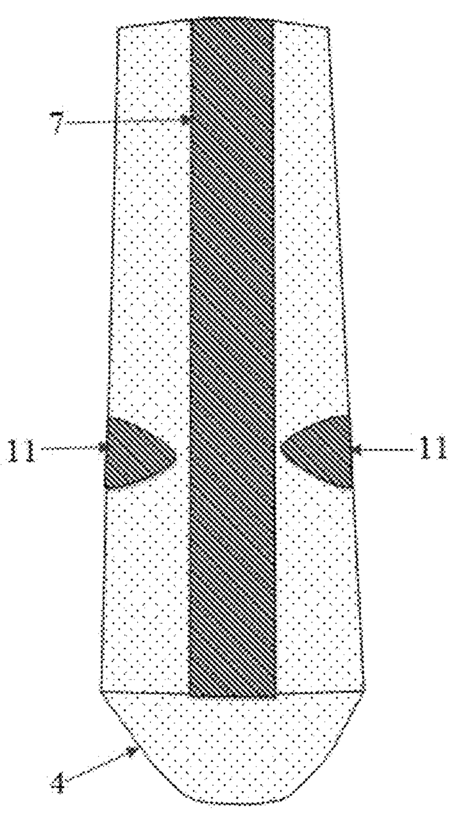
FIG. 5 is a volar view drawing of the embodiment shown in FIG. 4 of the inventive concepts disclosed herein.
Figure 6:
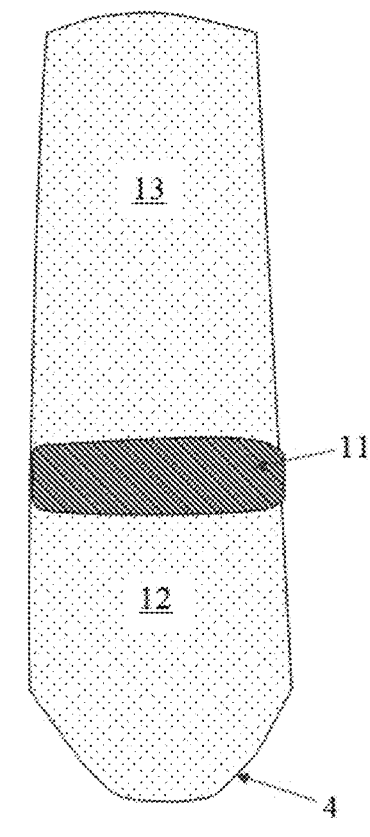
FIG. 6 is a dorsal view drawing of the embodiment shown in FIG. 4 of the inventive concepts disclosed herein.

An additional view, FIG. 4, illustrates the volar seam 7, angled transition at the joint line with the transverse seam 11, the straight, proximal tubular segment 12 and distal tubular segment 13, larger proximal opening 9 and smaller distal opening 10 to fit a human digit and an elongated dorsal flap 4 to assist with donning the device. A volar view, FIG. 5, illustrates the adhesive bonded or taped seam 7 and the elongated dorsal flap 4 to assist with donning the device. The volar extent of the adhesive bonded or taped transition seam 11 is visible at the level of the joint line. A dorsal view, FIG. 6, illustrates the adhesive bonded or taped transverse seam 11 where the elliptical piece of material has been removed dorsally in order to create the angled transition between the proximal straight tubular segment 12 and distal segment 13 and an elongated dorsal flap 4 to assist with donning the device.

Figures 7, 8, 9:
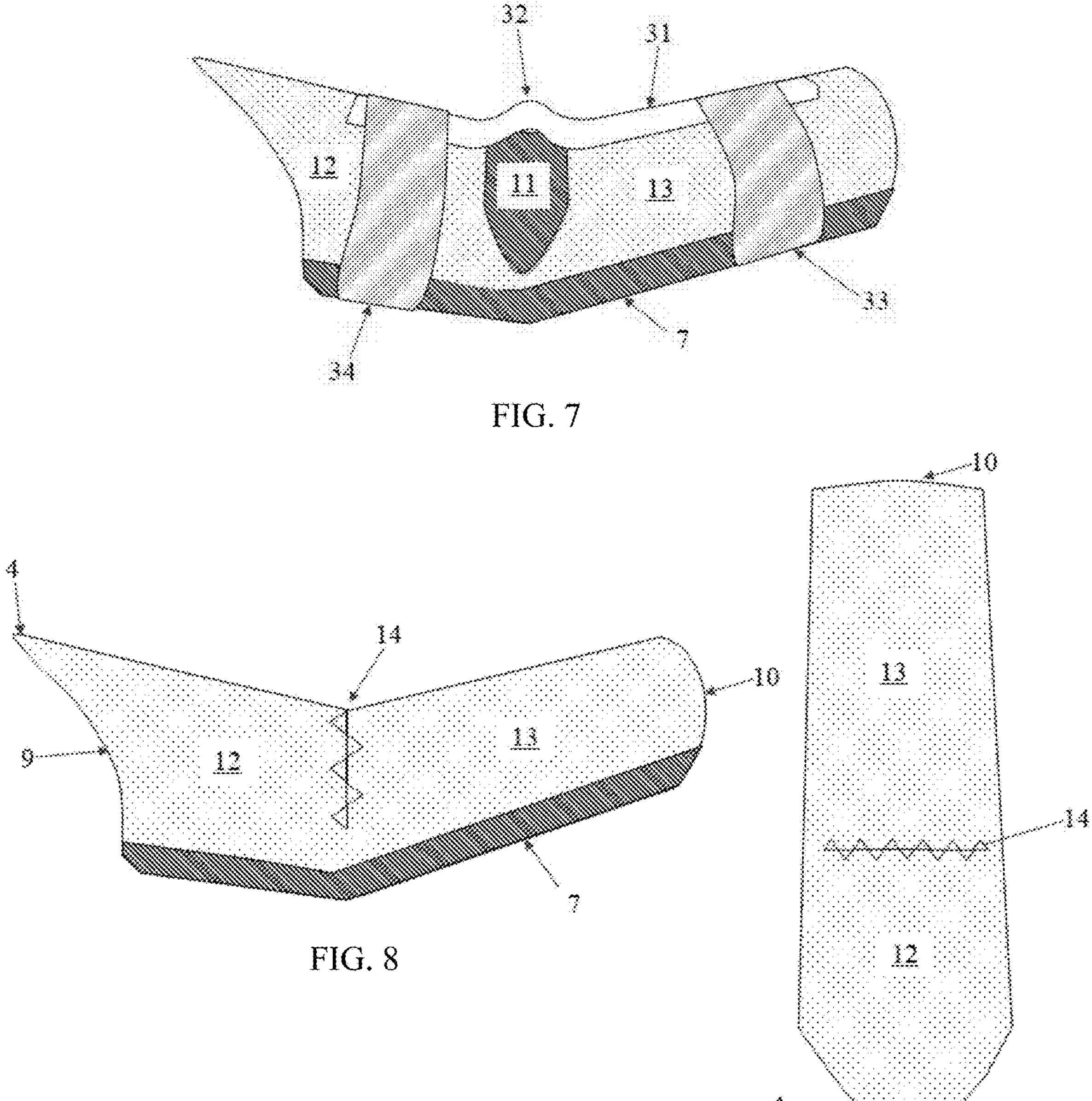
FIG. 7 is a side view drawing of one embodiment of the inventive concepts disclosed herein including a malleable element and securing circumferential straps.
FIG. 8 is a side view drawing of one embodiment of the inventive concepts disclosed herein with a sewn dorsal seam.
FIG. 9 is a dorsal view drawing of one embodiment shown in FIG. 8 of the inventive concepts disclosed herein with a sewn dorsal seam.

An alternative embodiment wherein the angled transition is created using a sewn dorsal seam 14 is illustrated in FIG. 8 and a dorsal view in FIG. 9 of this alternative embodiment wherein the sewn transition 14 is also seen.

Figure 10:
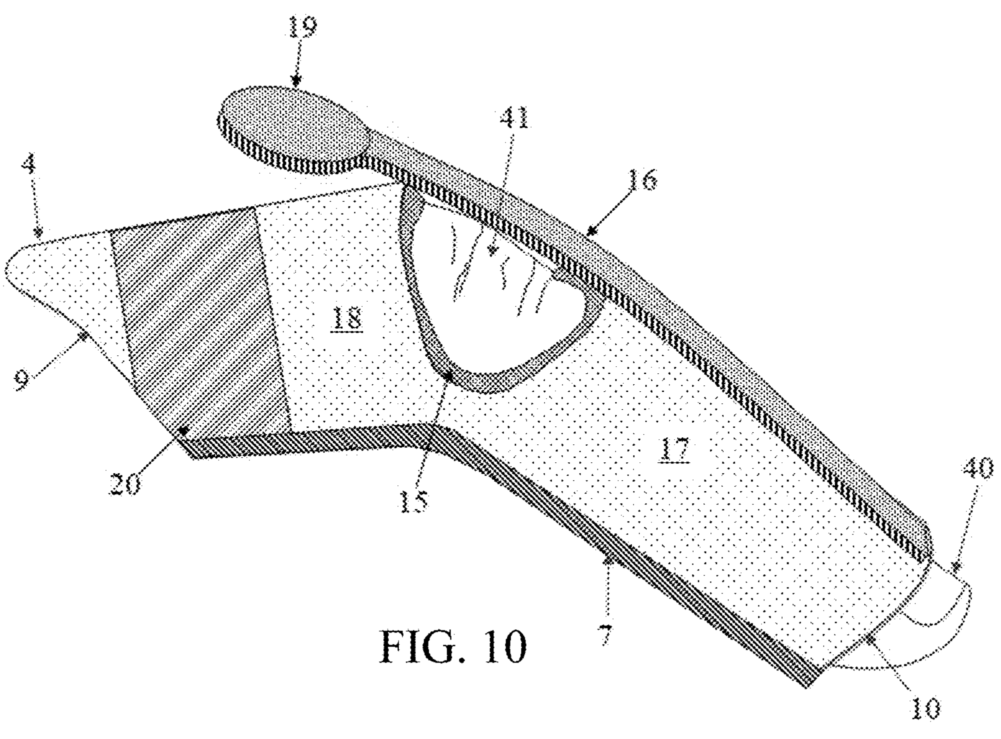
FIG. 10 is a side view drawing of one embodiment of the inventive concepts disclosed herein with the open transition design and dorsal tensioning element.

The devices thus described with a sewn or taped seam at the joint line can be difficult to don on digits with significant tightness of the interphalangeal joints (typically joint angles greater than 30 degrees). In order to address difficulty donning the device on a tightly contracted digit, an embodiment with an open transition design is illustrated in FIG. 10. The angled transition is left as an open ellipse 15 with the dorsal skin of the proximal interphalangeal joint exposed 41.

The fingertip is exposed 40 beyond the edge of the tapered distal tube segment 17. A dorsal strap element 16 is secured to the distal tube segment 17 using adhesive or heat-activated tape, but is not secured to the proximal tubular element 18. An enlarged tab 19 at the proximal end of the dorsal strap element aids in pulling and then securing the hook and loop material on the element's undersurface to the proximal tubular segment beneath. A cylindrical reinforcement 20 on the proximal tubular segment limits the segment from lifting off the dorsum of the finger once the dorsal strap is secured.

Figure 11:
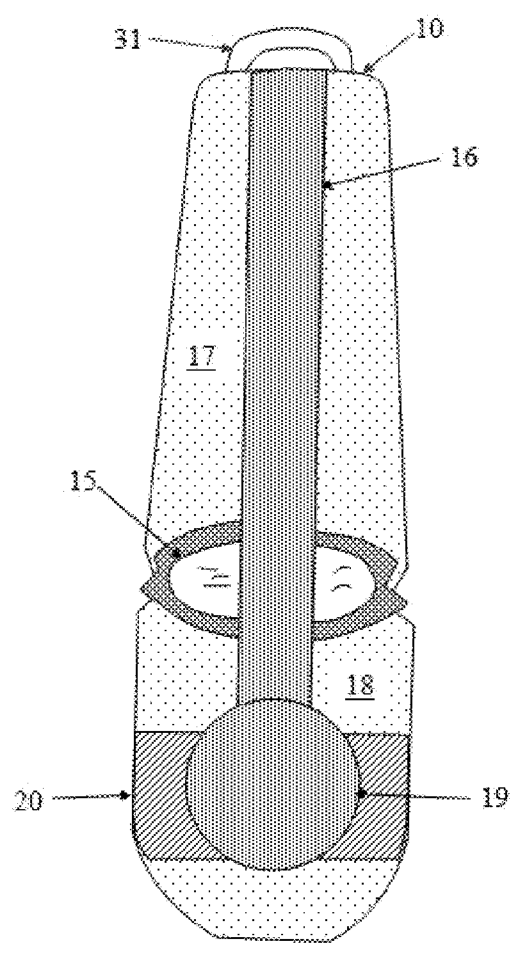
FIG. 11 is a dorsal view drawing of one embodiment shown in FIG. 10 of the inventive concepts disclosed herein with the dorsal tensioning element.

A dorsal view, FIG. 11, of the open transition design after securing the dorsal tab 19 to the proximal tubular segment in a tensioned manner to more closely approximate the edges of the open transition 15 thus providing the rotational force at the joint.

Figure 12:
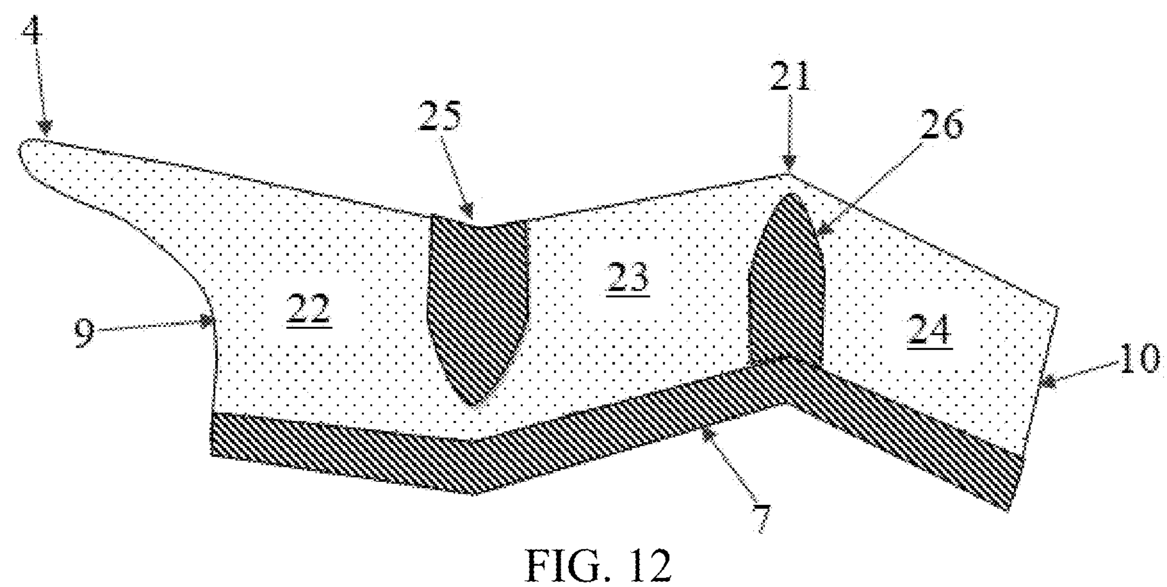
FIG. 12 is a side view drawing of one embodiment of the inventive concepts disclosed herein with angled transitions at both the proximal interphalangeal and distal interphalangeal joints.
Figure 13:
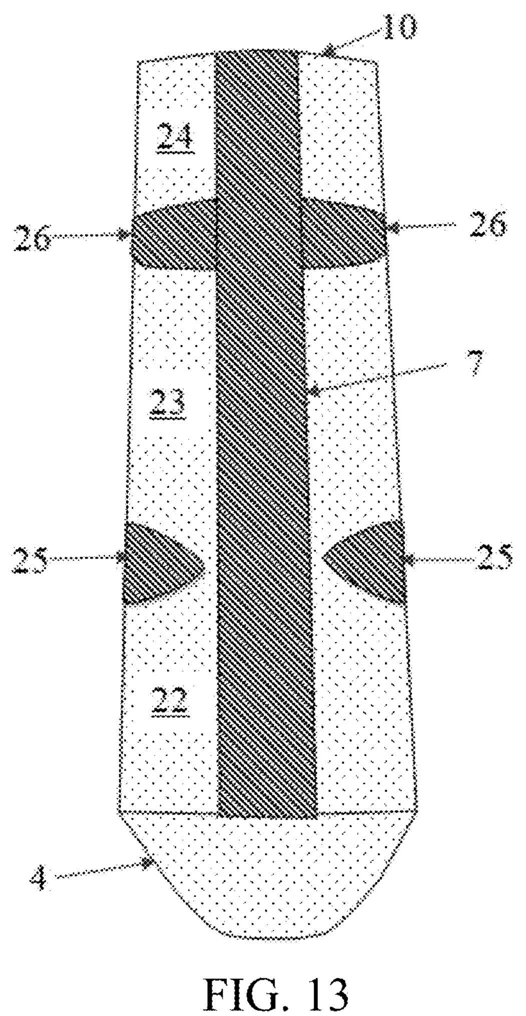
FIG. 13 is a dorsal view drawing of one embodiment shown in FIG. 12 of the inventive concepts disclosed herein with angled transitions at both the proximal interphalangeal and distal interphalangeal joints.

The devices thus described represent embodiments that create joint rotation using a single transition at the proximal interphalangeal joint. Certain congenital and acquired imbalances and contractures result in deformities at both the proximal and distal interphalangeal joints. An additional embodiment, FIG. 12, demonstrates the device constructed as described previously, but with an additional transition angle created at the distal interphalangeal joint 21. This embodiment demonstrates straight tubular elements over the proximal phalanx 22, middle phalanx 23, and distal phalanx 24. An adhesive bonded, taped, or sewn transverse seam at the proximal interphalangeal joint 25 and seam at the distal interphalangeal joint 26 create rotational forces at each joint. The volar view of this embodiment, FIG. 13, illustrates the volar extents of the adhesive bonded or taped transverse seam over the proximal joint 25 and over the distal joint 26.

Figure 14:
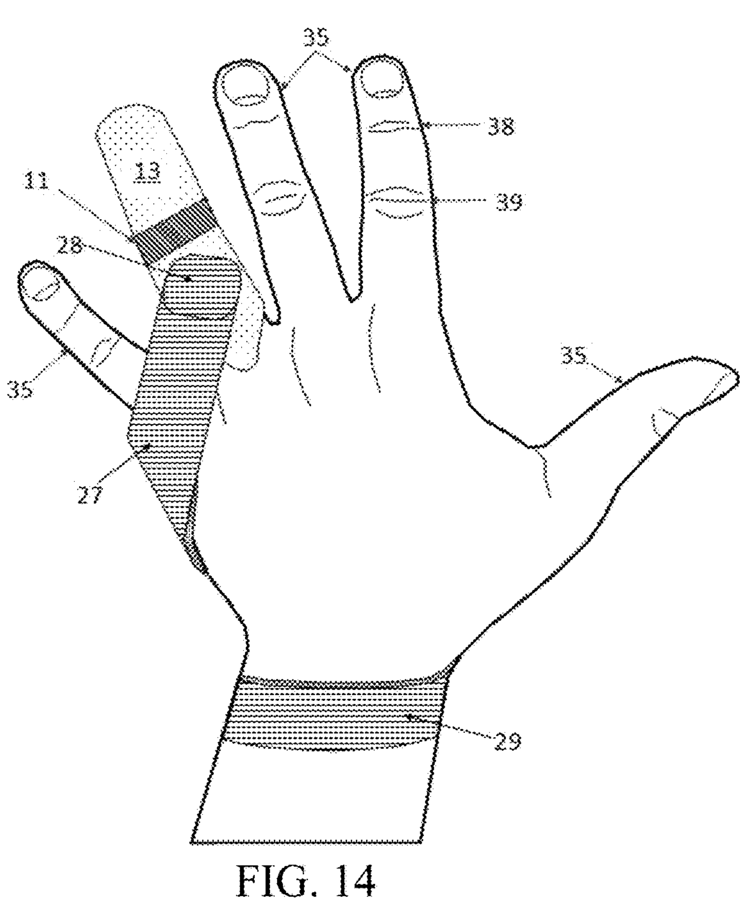
FIG. 14 is a dorsal view drawing of the retention strap in accordance with some embodiments of the inventive concepts disclosed herein
Figure 15:
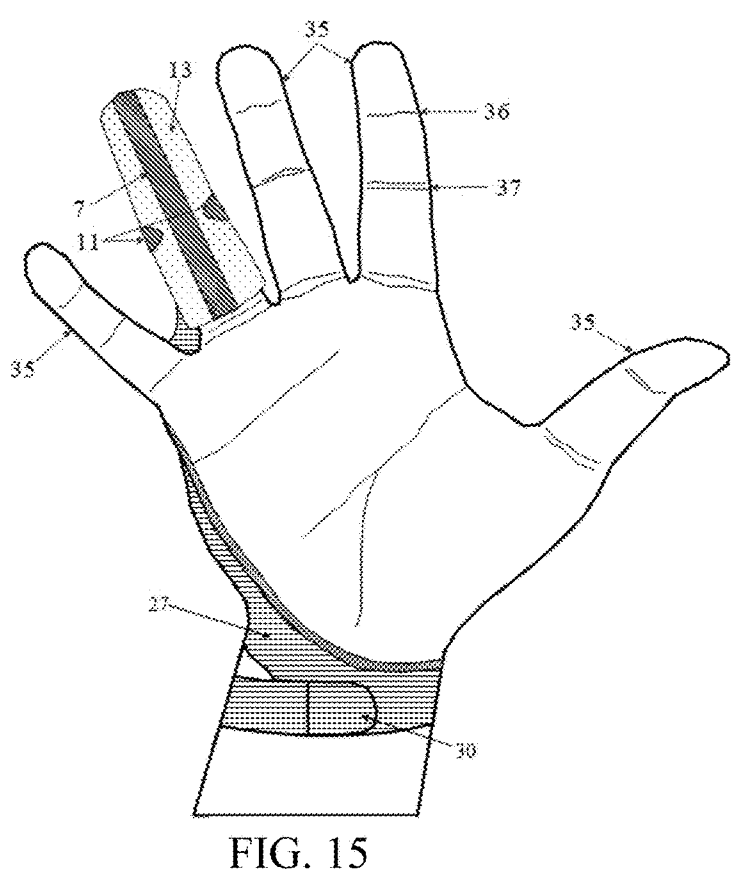
FIG. 15 is a volar view drawing of the retention strap in accordance with some embodiments of the inventive concepts disclosed herein

The devices thus described may be prescribed for wear over extended periods of time each day based upon the user's deformity and skin integrity. Device use at bedtime is facilitated by a neoprene retention strap, FIGS. 14,15. The strap 27 is secured to the dorsum of the device using a hook and loop material interface 28. The strap then wraps around the ulnar border of the palm, around the wrist 29 and is then secured to itself 30 using a hook and loop material interface.

Untreated digits 35 are not encumbered by the device. The skin creases on the volar surface of the distal interphalangeal joint 36 and proximal interphalangeal joint 37 and skin creases on the dorsal surface of the distal interphalangeal joint 38 and proximal interphalangeal joint 39 are illustrated in an untreated digit.

If a treating practitioner wishes to modify the force applied by the angled transition, a malleable element which is secured to the device is illustrated in FIG. 7. The malleable element 31 is made of a thermoplastic strip which is heat softened and upon cooling maintains its new shape. An elevated portion 32 of the malleable element is created to reduce pressure of the element on the skin on the dorsum of the digit at the joint level. A looped fabric strap 33 secures the malleable element over the distal tubular segment and a looped fabric strap 34 secures the malleable element to the proximal tubular segment.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the inventive concepts disclosed herein. The order or sequence of any operational flow or method operations may be varied or re-sequenced according to alternative embodiments. Other substitutions, modifications, changes, and omissions may be made in the design, operating conditions and arrangement of the exemplary embodiments without departing from the broad scope of the inventive concepts disclosed herein.

Terminology

"Volar" refers to the palmar or plantar surface of the hand

"Dorsal" refers to the side opposite the volar surface

"Proximal" refers to closer to the center axis of the body

"Distal" refers to further away from the center axis of the body

"Interphalangeal joints" referring to the joints between the proximal, middle, and distal phalanges of the digits of the hand "Digit" a finger or thumb "Don" refers to the placement of a splint or garment on a body part "Doff" refers to the removal of a splint or garment

What is claimed is:

1. A device configured to produce a rotational force at one or more interphalangeal joints of a digit, the device comprising:

a tubular component formed from a sheet of stretchable material and configured to extend over adjacent phalanges of the digit;

one or more elliptical-shaped cutouts located within the sheet of stretchable material;

one or more seams adapted to fasten opposing edges of each of the one or more elliptical-shaped cutouts such upon that the one or more elliptical-shaped cutouts are closed, the tubular component defining one or more angular transitions;

wherein the one or more angular transitions are adapted to overlie the one or more interphalangeal joints when the device is applied over the digit, and wherein the one or more angular transitions are configured to create a rotational force at the one or more interphalangeal joints.

2. The device as in claim 1 wherein the device is configured with a smooth interior surface, the smooth surface configured to provide circumferential contact of the stretchable material with the digit in order to produce a compressive force.

3. The device as in claim 1 wherein the device further comprises a malleable, angled element wherein the malleable, angled element is configured to modify the rotational force at the interphalangeal joint.

4. A device configured to produce a rotational force at one or more interphalangeal joints of a digit, the device comprising:

a tubular component formed from a sheet of stretchable material configured to extend over adjacent phalanges of the digit;

at least one opening in the tubular component adapted to overlie the one or more interphalangeal joints when the device is applied over the digit wherein, after placement on the digit, a strap is subsequently configured to be secured across the at least one opening in the sheet of stretchable material and adapted to create a rotational force at the one or more interphalangeal joints.

5. The device as in claim 4 wherein the device is configured with a smooth interior surface, the smooth surface configured to provide circumferential contact of the stretchable material with the digit in order to produce a compressive force.

6. The device as in claim 4 wherein the device further comprises a malleable, angled element wherein the malleable, angled element is configured to modify the rotational force at the interphalangeal joint.

7. An orthotic device for use with one or more interphalangeal joints of a finger, the orthotic device comprising:

a sheet of neoprene joined lengthwise to itself at an edge so as to form a tubular component configured to extend over the phalanges of the finger adjacent to an one or more interphalangeal joints;

one or more elliptical-shaped cutouts formed within the sheet of the stretchable material;

one or more seams adapted to fasten opposing edges of each of the one or more elliptical-shaped cutout such that upon the one or more elliptical shaped cutouts are closed, the tubular component defining one or more angular transitions;

wherein the one or more angular transitions are configured to create a rotational force at the one or more interphalangeal joints; and wherein the tubular component is configured to fit the finger.

8. The device as in claim 7 wherein the orthotic device is configured with a smooth interior surface, the smooth surface providing circumferential contact of the sheet of neoprene with the finger and producing a compressive force.

9. The device as in claim 7 wherein the orthotic device further comprises a malleable, angled element configured to modify the rotational force at the interphalangeal joint.

* * * * *